United States Patent
Dailey

(10) Patent No.: US 11,607,020 B2
(45) Date of Patent: Mar. 21, 2023

(54) PENDANT SYSTEM WITH PENDANT GENERATING HAPTIC FEEDBACK

(71) Applicant: Todd Dailey, Westfield, IN (US)

(72) Inventor: Todd Dailey, Westfield, IN (US)

( * ) Notice: Subject to any disclaimer, the term of this patent is extended or adjusted under 35 U.S.C. 154(b) by 441 days.

(21) Appl. No.: 16/837,334

(22) Filed: Apr. 1, 2020

(65) Prior Publication Data

US 2021/0307462 A1 Oct. 7, 2021

(51) Int. Cl.
| | | |
|---|---|---|
| A44C 25/00 | (2006.01) | |
| G06F 3/01 | (2006.01) | |
| G06F 1/16 | (2006.01) | |
| A61B 5/00 | (2006.01) | |
| A61B 5/024 | (2006.01) | |
| G08B 21/24 | (2006.01) | |

(52) U.S. Cl.
CPC ........ *A44C 25/001* (2013.01); *A61B 5/02438* (2013.01); *A61B 5/6802* (2013.01); *A61B 5/7455* (2013.01); *G06F 1/163* (2013.01); *G06F 3/016* (2013.01); *G08B 21/24* (2013.01); *A61B 5/6822* (2013.01)

(58) Field of Classification Search
CPC .................................................. G08B 21/24
See application file for complete search history.

(56) References Cited

U.S. PATENT DOCUMENTS

| | | | |
|---|---|---|---|
| D299,779 S | 2/1989 | Kohen et al. | |
| 6,326,881 B1 * | 12/2001 | Dahl | G04G 13/02 340/309.5 |
| 8,983,551 B2 | 3/2015 | Worick et al. | |
| 9,177,307 B2 | 11/2015 | Ross et al. | |
| 2005/0233775 A1 | 10/2005 | Chang | |
| 2006/0177806 A1 | 8/2006 | Parsons | |
| 2007/0087790 A1 * | 4/2007 | Worick | H04M 19/041 455/567 |
| 2008/0101160 A1 | 5/2008 | Besson | |
| 2010/0204541 A1 * | 8/2010 | Balian | A61M 21/00 600/27 |
| 2015/0290075 A1 | 10/2015 | Calisir | |
| 2015/0374079 A1 | 12/2015 | Zebley | |
| 2016/0063890 A1 | 3/2016 | Sethi | |
| 2017/0003720 A1 * | 1/2017 | Robinson | G06F 1/1632 |
| 2017/0316674 A1 * | 11/2017 | Candy | G08B 21/24 |
| 2020/0022599 A1 * | 1/2020 | Yin | A61B 5/002 |

FOREIGN PATENT DOCUMENTS

GB 2424083 A 9/2006

* cited by examiner

*Primary Examiner* — Kam Wan Ma
(74) *Attorney, Agent, or Firm* — Maginot, Moore & Beck LLP

(57) ABSTRACT

A pendant system includes a pendant, a vibration element, and a controller. The pendant is configured to mount on a necklace. The pendant includes a housing. The vibration element is located within the housing and is configured generate haptic feedback when activated. The controller is located within the housing and is configured to activate the vibration element randomly.

20 Claims, 6 Drawing Sheets

PENDANT SYSTEM WITH PENDANT GENERATING HAPTIC FEEDBACK

FIELD

This disclosure relates to the field of jewelry and, in particular, to a pendant providing the wearer with haptic feedback.

BACKGROUND

In a world where our senses are increasingly overwhelmed by the flood of omnipresent screens and optimized media material, people are struggling more than ever to step back and operate from a balanced, mindful state. Every day we find ourselves making decisions and taking actions that do not align with our core beliefs or values, realized only at the end of the day or even week, as our minds briefly and temporarily unwind from the rushed chaos of the workday. Unfortunately, these mishaps compound on one another. Just as when a freshly-washed car hits that first mud puddle, the value of avoiding the next mud puddle drops drastically. Before we know it we can find ourselves in a downward spiral that will not only have worldly implications (stress, failure, unhappiness), but for the many with spiritual beliefs, the mishaps could have eternal ramifications.

Maintaining a balanced state amidst the infinite distractions and sensory overload that consume our day to day is difficult. Many known devices that attempt to accomplish this feat have seen mixed results as they add yet another isolated 'task' in an already complicated and time constrained lifestyle. For at least these reasons, products that can leverage core motivations to help naturally and simplistically realign and re-center thoughts and emotions (without introducing additional burdens and obligations), are much needed.

SUMMARY

According to an exemplary embodiment of the disclosure, a pendant system includes a pendant, a vibration element, and a controller. The pendant is configured to mount on a necklace. The pendant includes a housing. The vibration element is located within the housing and is configured generate haptic feedback when activated. The controller is located within the housing and is configured to activate the vibration element randomly.

According to another exemplary embodiment of the disclosure, an accessory system for a pendant of a necklace includes a housing, a vibration element, and a controller. The housing is configured for mounting on the pendant. The vibration element is located within the housing and is configured to generate haptic feedback when activated. The controller is located within the housing and is configured to activate the vibration element randomly.

According to a further exemplary embodiment of the disclosure a method of operating a pendant system including a pendant mounted on a necklace includes adjusting a length of the necklace to position the pendant against the chest of a user wearing the necklace; and randomly activating a vibration element located within a housing of the pendant to generate haptic feedback felt with the chest of the user. The controller is located within the housing and is configured to activate the vibration element.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
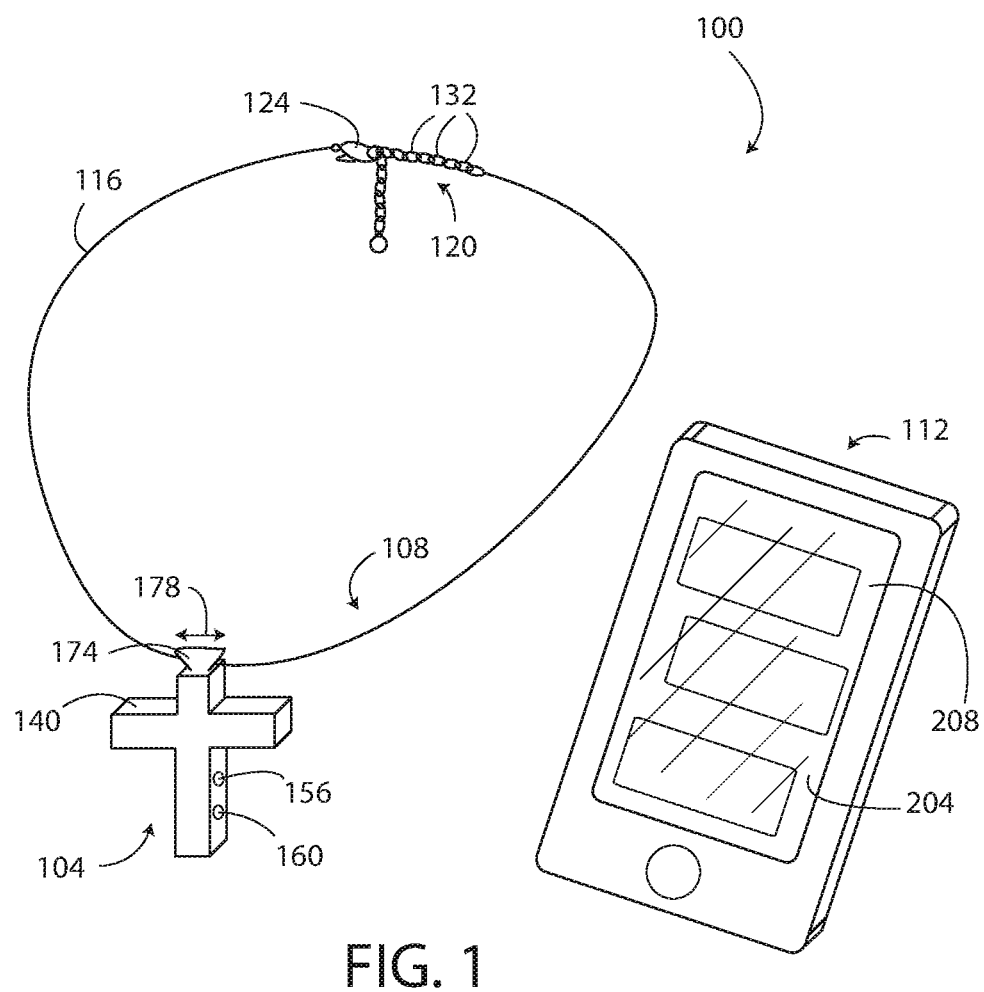
FIG. 1 is a block diagram of a pendant system, as disclosed herein, including a pendant mounted on a necklace and a remote electronic device shown as a smartphone.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Aspects of the disclosure are disclosed in the accompanying description. Alternate embodiments of the disclosure and their equivalents may be devised without parting from the spirit or scope of the disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

As shown in FIG. 1, a pendant system 100 includes a pendant 104 slidably mounted on a necklace 108 and a remote electronic device shown as a smartphone 112. In some embodiments, the pendant 104 is a "21$^{st}$ century crucifix" or a "smart crucifix" that corresponds to a wearer's religious faith or spirituality focus. The pendant 104 is configured to generate haptic feedback transmitted to a user of the system 100. The terms "user" and "wearer" are used synonymously herein. The haptic feedback, which is generated near the user's heart, reminds the user of their core values and beliefs, what is at stake spiritually, and encourages them to re-center their mindset. The prior art has struggled to accomplish this feat because the prior art has left out two integral considerations that are core mindfulness motivators for billions of people in the world: human anatomy and faith.

First, human anatomy—experts have very often characterized the mindfulness challenge as finding balance in operating between your head (cognitively) and your heart. The ability for a 'reminder' to be felt in very close proximity to the heart organ (where we find our balance), is paramount to inciting motivation for the user to truly take notice.

Second, faith (i.e. spirituality, religion)—billions of people in this world associate with some sort belief system that drives much of their perceived purpose on earth. Having a healthy spiritual life is one that in most cases, has implications even beyond this life. When people are reminded to operate in a balanced state within the context of their spirituality, the motivation is exponentially greater than an isolated request to 'breath,' 'meditate,' or 'exercise'. While those are valuable steps indeed, and are a component of the pendant system 100, they are the 'what' and not the 'why' that motivation must start with.

Moreover, the pendant system 100 ties together the two considerations set forth above in a fashion that is extremely simplistic, such that no additional burdens are placed on a user who is already mentally fatigued with the stresses of daily life. Specifically, the pendant system 100 operates automatically and without creating additional distractions to the user. Each element of the pendant system 100 and a method 400 (FIG. 4) for operating the pendant system 100 are described herein.

The necklace 108 is configured to be worn around a user's neck to place the pendant 104 near the heart of the user and against the chest of the user. In one embodiment, the necklace 108 includes a chain 116, an adjustable link portion 120, and a clasp 124. The chain 116 is formed from any desired material including metals such as gold and silver, as well as metals plated with gold and silver. The chain 116 may also include or be formed steel. In other embodiments, the chain 116 is formed from plastic, silicon, natural fibers, and/or artificial fibers. As such, in some embodiments, the chain 116 is elastic and may be stretched to fit over the user's head.

The adjustable link portion 120 includes a plurality of links 132 chained together. The link portion 120 may include from five to twenty of the links 132 serially connected. In other embodiments, the link portion 120 includes only one of the links 132.

The clasp 124 is configured to connect to a selected one of the links 132 of the adjustable link portion 120. The clasp 124 is provided as a lobster claw, a spring-ring, a fishhook, a fold-over, or any other typical necklace clasp style. An effective length of the necklace 108 is adjusted based on the selected link 132 that is connected to the clasp 124. In other embodiments, the necklace 108 has a fixed length and does not have an adjustable length.

Figure 2:
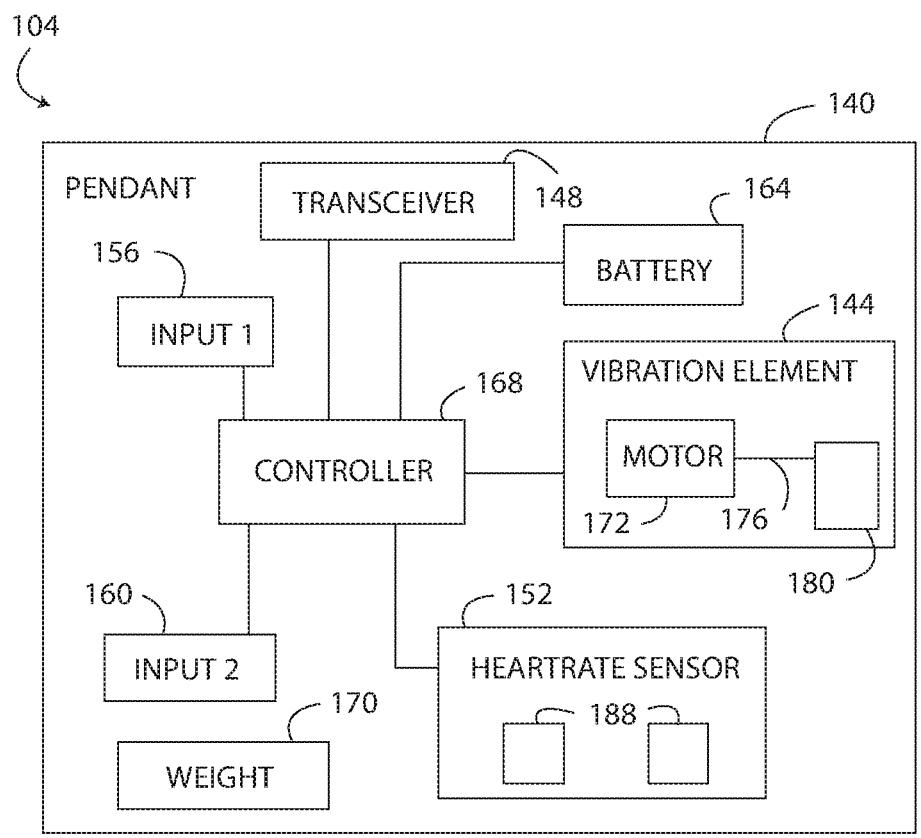
FIG. 2 is a block diagram of the pendant of FIG. 1.

As shown in FIG. 2, the pendant 104 includes a housing 140 having a vibration element 144, a transceiver 148, a heartrate sensor 152, a first input 156, a second input 160, and a battery 164 each operably connected to a controller 168. Typically, the shape of the housing 140 is one that has a special meaning to the user of the pendant system 100. As such, the housing 140 may have a shape based on religion, spirituality, love, and friendship. In an exemplary embodiment, the housing 140 is shaped as a cross (shown in FIG. 1), a crucifix, a peace sign, or a Star of David. In some embodiments, the housing 140 is waterproof, such that the pendant 104 is wearable while the user is swimming or in a shower without damaging the pendant 104 including without damaging the controller 168 and the vibration element 144. It is appreciated that additional components (not shown) may further be provided to facilitate functioning of the pendant 104. In addition, one or more of the listed components of the pendant 104 may be omitted and/or provided in additional devices in communication with those listed herein.

The housing 140 is sized to be small and compact, such that the wearer typically will not notice that they are wearing the necklace 108 and pendant 104, except, of course, when the pendant 104 generates the haptic feedback. An exemplary housing 140 is from about one to five centimeters long, from about 0.5 to four centimeters wide, and from about three to twenty millimeters thick. Typically, the housing 140 is as low profile and compact as is reasonable, without inhibiting the wearer from feeling the haptic feedback. In other embodiments, the housing 140 has any size as is desired and as may be used to accommodate the components positioned therein.

The housing 140 of the pendant 104 is configured to remain positioned against the user's chest so that the haptic feedback generated by the vibration element 144 is transferred effectively and efficiently to the user. In one embodiment, the housing 140 further includes a weight 170 (FIG. 2) that uses gravity to pull the pendant 104 against the user. Additionally or alternatively, the electronic components within the housing 140, such as the battery 164, are positioned within the housing 140 to pull the pendant 104 against the user. For example, in the cross-shaped housing 140 of FIG. 1, the battery 164 is positioned at the bottom or the back of housing 140 to use the weight of the battery 164 in maintaining the housing 140 against the user.

As shown in FIG. 1, the pendant 104 further includes a loop 174 extending from the housing 140 and through which the necklace 108 passes to mount the housing 140 on the necklace 108. A width 178 of the loop 174 is selected to position pendant 104 properly against the chest of the wearer so that the wearer feels the haptic feedback. An exemplary width 178 of the loop 174 is approximately five to fifteen millimeters depending, at least in part, on the size and shape of the housing 140. Moreover, since the width 178 of the loop 174 is comparatively wide compared to the housing 140, the loop 174 prevents the pendant 104 from moving out of position in response to movements of the wearer. Therefore, the loop 174 further assists in positioning the pendant 104 properly against the wearer so that the wearer feels the haptic feedback generated by the vibration element 144. In other embodiments, any other style and width of the loop 174 is provided to mount the pendant 104 on the necklace 108.

The vibration element 144, which is also referred to herein a mechanical vibrator, is configured generate haptic feedback to a user of the pendant system 100. The vibration element 144, in an exemplary embodiment, includes an electric motor 172 with a corresponding driveshaft 176. An unbalanced mass 180 is mounted on the driveshaft 176. Rotation of the driveshaft 176 spins the unbalanced mass 180 and generates the haptic feedback. In other embodiments, the pendant 104 includes any other suitable type of vibration element 144.

The transceiver 148, which is also referred to as a wireless transmitter and receiver, is configured to transmit wirelessly data from the pendant 104 to the smartphone 112 and to receive wirelessly data from the smartphone 112. The transceiver 148 sends and receives data using a wireless local area network ("Wi-Fi"), a personal area network, and/or any other wireless network. Accordingly, the transceiver 148 is compatible with any desired wireless communication standard or protocol including, but not limited to, Near Field Communication ("NFC"), IEEE 802.11, and IEEE 802.15.1 ("Bluetooth®"), for example.

With continued reference to FIG. 2, the heartrate sensor 152 is configured to generate heartrate data corresponding to a measured heartrate of a person wearing the pendant 104 and the necklace 108. The heartrate sensor 152 includes electrodes 188 that are positioned against or near the skin of the user. The heartrate sensor 152 senses a pulse of the user and/or senses electrocardiogram data (EKG data) of the user. In some embodiments, the pendant 104 does not include the heartrate sensor 152.

The first input 156 is a user interface device for activating and deactivating the pendant 104. In particular, the first input 156 is a switch or a button that is moved or pressed by the user of the pendant system 100. For example, when the first input 156 is pressed a first time, the pendant system 100 "powers on" and is activated, and when the first input 156 is pressed a second time, the pendant system 100 "powers off" and is deactivated.

The second input 160 is another user interface device for "pairing" the pendant 104 to the smartphone 112. In particular, the second input 160 is a switch or a button that is moved or pressed by the user of the pendant system 100. For example, when the second input 160 is pressed, the pendant 104 and the smartphone 112 share data wirelessly for pairing the pendant 104 with the smartphone 112.

The battery 164 is a rechargeable lithium-ion polymer (Li-ion polymer or LiPo) battery cell having a nominal voltage of about 3.7 V. In other embodiments, the battery 164 is a nickel-cadmium (NiCd), nickel-metal hydride (NiMH), lithium-ion (Li-ion), or any other desired rechargeable battery architecture. In one embodiment, the battery 164 requires recharging only after five to seven days of continuous use of the pendant system 100. Thus, the pendant system 100 requires infrequent recharging as a convenience to the user. In yet another embodiment, the battery 164 is a button cell battery, also referred to herein as a watch battery, and the housing 140 has a corresponding structure to permit user removal and user replacement of the button cell battery 164. Typically, embodiments of the pendant system 100 that include the button cell battery 164 operate continuously for at least two to four months without requiring a battery charge or a battery replacement. An exemplary button cell battery 164 for use with the pendant system 100 is model 2016 or 2032.

The controller 168 of the pendant 104 is configured to execute program instructions (i.e. software) for operating the system 100 to generate haptic feedback to the user, to transmit and receive data from the smartphone 112, and to recharge the battery 164. Additionally, in some embodiments, the controller 168 generates activation signals for activating the vibration element 144. The controller 168 is provided as at least one microcontroller and/or microprocessor.

Figure 3:
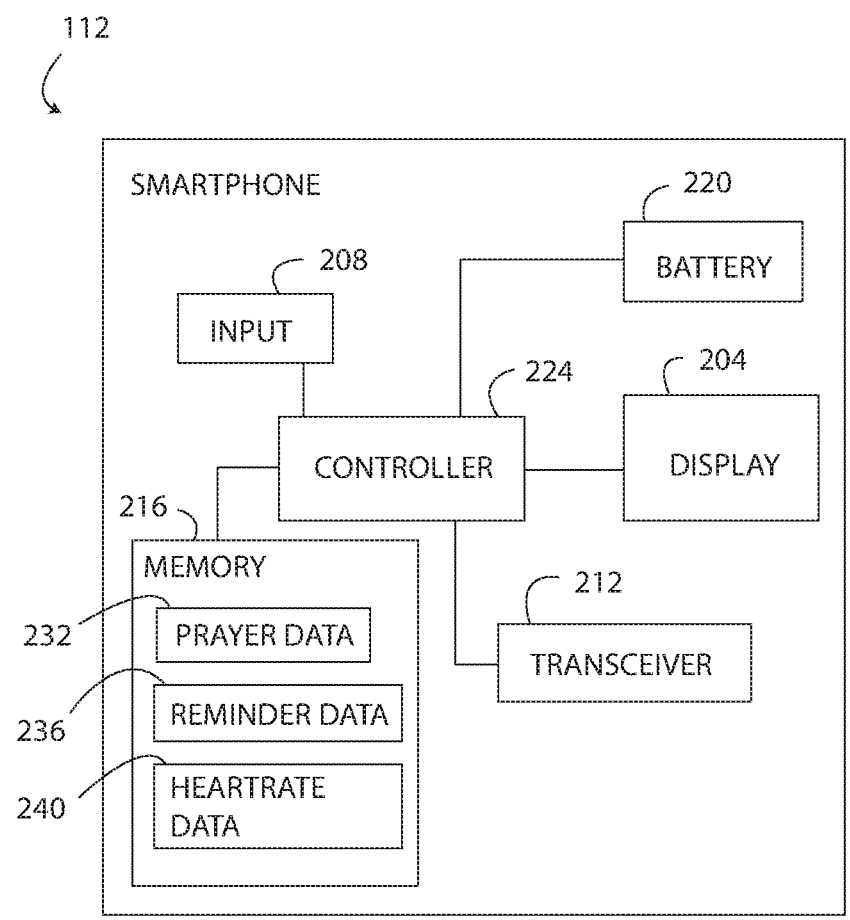
FIG. 3 is a block diagram of the smartphone of FIG. 1.

As shown in FIG. 3, the smartphone 112 is an exemplary remote electronic device that is operably connected to the pendant 104. The smartphone 112 includes a display unit 204, an input unit 208, a transceiver 212, a memory 216, and a battery 220, each of which is operably connected to a controller 224. It is appreciated that additional components (not shown) may further be provided to facilitate functioning of the smartphone 112. In addition, one or more of the listed components of the smartphone 112 may be omitted and/or provided in additional devices in communication with those listed herein.

The display unit 204, in one embodiment, is a liquid crystal display (LCD) panel configured to display text, images, and other visually comprehensible data. The display unit 204, in another embodiment, is any display unit as desired by those of ordinary skill in the art, including, but not limited to, an active-matrix organic light-emitting diode display. The display unit 204 is configurable to display, for example, one or more interactive interfaces or display screens, including a display of a prayers, meditation guides, breathing guides, and/or pictures.

The input unit 208 is configured to receive data input via manipulation by a user of the pendant system 100. The input unit 208 may be configured as a touchscreen applied over the display unit 204 that is configured to enable a user to input data via the touch of a finger and/or a stylus. In another embodiment, the input unit 208 comprises any device configured to receive input data, as may be utilized by those of ordinary skill in the art, including, for example, one or more buttons, switches, keys, microphones, and/or the like. The input unit 208 is also referred to herein as a user input.

The transceiver 212, which is also referred to as a wireless transmitter and receiver, is configured to transmit wirelessly data from the smartphone 112 to the pendant 104 and to receive wirelessly data from the pendant 104. The transceiver 212 sends and receives data using a wireless local area network ("Wi-Fi"), a personal area network, and/or any other wireless network. Accordingly, the transceiver 212 is compatible with any desired wireless communication standard or protocol including, but not limited to, Near Field Communication ("NFC"), IEEE 802.11, and IEEE 802.15.1 ("Bluetooth®"), for example.

The memory 216, as shown in FIG. 3, is an electronic data storage unit, which is also referred to herein as a non-transient computer readable medium. In one embodiment, the memory 216 is configured to store prayer data 232, reminder data 236, and heartrate data 240, among any other data for operation of the pendant system 100.

The prayer data 232, when processed by the controller 224 of the smartphone 112, causes the display unit 204 to display a prayer, a biblical verse, and/or a religious text. The specific texts/prayers included in the prayer data 232 is customizable by the user of the pendant system 100. Exemplary prayers included in the prayer data 232 include The Lord's Prayer, Hail Mary, Glory Be, and The Apostles' Creed. Any other prayer or any text that is meaningful to the user of the pendant system 100 may also be included in the prayer data 232, and the prayer data 232 is exemplary user-created data.

The reminder data 236, which is also referred to herein as activity data, when processed by the controller 224 of the smartphone 112, cause the display unit 204 to display a reminder to execute a breathing exercise, a reminder to meditate, and/or a reminder to re-center and to focus on matters of mental health and spiritual development. For example, the reminder data 236 may result in the display unit 204 displaying a message stating that the user should take ten deep breaths or that the user should meditate for the next two to five minutes. The reminder data 236 is exemplary user-created data.

The heartrate data 240 includes data generated by the heartrate sensor 152 of the pendant 104 that has been transmitted from the pendant 104 from the smartphone 112. The heartrate data 240 includes data corresponding to the number of beats per minute of the user's heart, for example. The heartrate data 240 may also include EKG data depending on the type of heartrate sensor 152 included in the pendant 104. Moreover, the heartrate data 240 may include data corresponding to a predetermined heartrate range. An exemplary predetermined heartrate range is from 130 to 150 beats per minute.

The battery 220 of the smartphone 112 is a rechargeable lithium-ion polymer (Li-ion polymer or LiPo) battery cell having a nominal voltage of about 3.7 V. In other embodiments, the battery 220 is a nickel-cadmium (NiCd), nickel-metal hydride (NiMH), lithium-ion (Li-ion), or any other desired rechargeable battery architecture.

The controller 224 of the smartphone 112 is configured to execute program instructions (i.e. software, an application, or an "app") for operating the system 100 to generate haptic feedback to the user, to transmit and receive data from the pendant 104, and to recharge the battery 220. Additionally, in some embodiments, the controller 224 generates activation signals, transmitted to the pendant 104, for activating the vibration element 144. The controller 224 is provided as at least one microcontroller and/or microprocessor.

Figure 4:
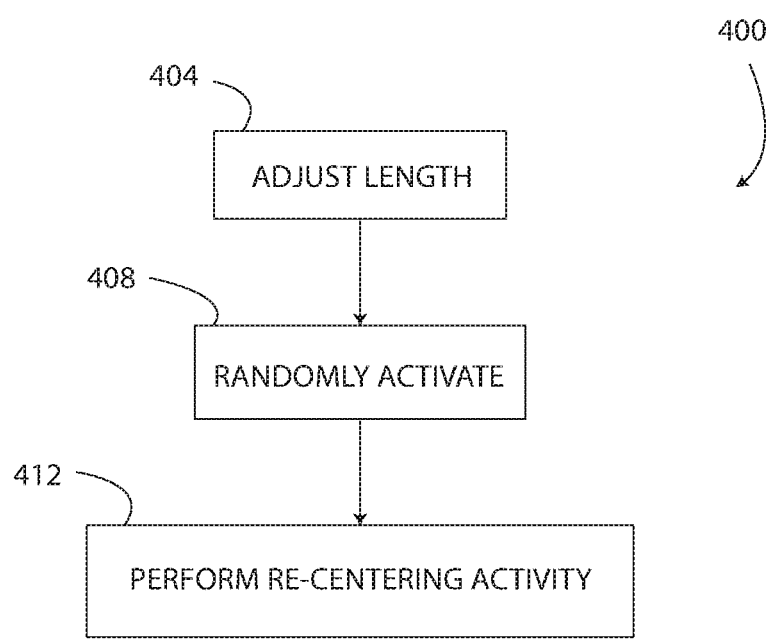
FIG. 4 is a flowchart illustrating an exemplary method of operating the pendant system of FIG. 1.

With reference to FIG. 4, the pendant system 100 is configured to perform a method 400 for assisting the user in re-centering their thoughts and efforts. In short, the pendant 104 is configured to generate randomly the haptic feedback. Upon feeling the haptic feedback, the user is reminded of any matter of personal importance, such as re-centering their thoughts and/or focusing on faith. After being reminded, the user may decide to perform a re-centering activity with or without viewing the display unit 204 of the smartphone 112. The method 400 is described in detail herein.

In block 404, the method 400 includes adjusting a length of the necklace 108 and placing the necklace 108 around the neck of the user. Specifically, the user adjusts the length of the necklace 108 to position the pendant 104 against their chest. The length of the necklace 108 is adjusted by selecting a link 132 to connect to the clasp 124. In embodiments of the pendant system 100 that include a necklace 108 having a fixed length, this portion of the method 400 is omitted, and the necklace 108 is simply placed around the neck of the user. Typically, the length of the necklace 108 places the pendant 108 near the heart of the user.

Next, the user powers on the pendant 104 using the input 156, so that the controller 168 is supplied with electrical energy from the battery 164. The pendant 104 is powered on either before or after the user wears the necklace 108. After the pendant 104 is powered on, the user continues their normal daily activities. The pendant 104 and the necklace 108 do not inhibit the activities performed by the user. For example, the user may decide to shower, bath, or swim, and the housing 140 of the pendant 104 is waterproof to prevent damage to the components within the housing 140. Moreover, the user may decide to exercise or engage in other physical activities while wearing the necklace 108 and pendant 104. There is no requirement to keep the smartphone 112 near the pendant 104 during use of the system 100 because activation signals for activating the vibration element 144 are generated by either controller 168 of the pendant 104 or the smartphone 112.

In block 408, the method 400 includes randomly activating the vibration element 144 to generate the haptic feedback. In the embodiment illustrated in FIG. 1, the random activation signals are randomly generated by the smartphone 112. As used herein, the random generation of the activation signals includes randomly generating the activation signals a predetermined number of times within a predetermined time period. For example, in one embodiment, the predetermined time period is ten hours and the predetermined number of times is five. Thus, in this example, the activation signals are randomly generated by the smartphone 112 five times in a ten-hour time period. In this embodiment, there is no fixed schedule for generating the activation signals within the ten-hour time period. Thus, the activation signals are randomly generated.

Block 408 of the method 400 also includes transmitting the activation signals from the smartphone 112 to the pendant 104. The activation signals are transmitted using the transceiver 212 of the smartphone 112, and the activation signals are received by the transceiver 148 of the pendant 104. In one embodiment, the pendant 104 and the smartphone 112 use the Bluetooth® protocol to transmit and to receive the activation signals. The activation signals are typically transmitted by the smartphone 112 to pendant 104 as soon as they are generated.

When an activation signal transmitted by the smartphone 112 is received by the pendant 104, the pendant 104 is configured to activate the vibration element 144 in order to generate the haptic feedback. Specifically, the transceiver of the pendant 104 is configured to send the received activation signal to the controller 168 for activating the vibration element 144 randomly. That is, the vibration element 144 is activated in the same random way that the smartphone 112 generates the random activation signals, and the controller randomly activates the vibration element a predetermined number of times within a predetermined time period. The predetermined number of times and the predetermined time period are the same as the predetermined number of times and the predetermined time period that the activation signals are generated by the smartphone 112. Activation of the vibration element 144 includes suppling electrical energy to the motor 172 and causing the driveshaft 176 to rotate the unbalanced mass 180.

Since, the vibration element 144 is activated randomly, the user is typically unaware of when the pendant 104 will generate the haptic feedback. Moreover, as stated above, the user typically feels the haptic feedback when the housing 140 of the pendant 104 vibrates against the user's chest near their heart.

The vibration element 144, in response to receiving the activation signal, generates a single vibration pulse that last from 0.5 seconds to three seconds. Additionally, in some embodiments, the vibration element 144 is configured to generate a varying vibration pattern, which is also referred to herein as a haptic feedback sequence. For example, in one embodiment, the haptic feedback sequence is a pulsed vibration having from two to five vibration pulses of equal duration. The controller 168 randomly selects the number of vibration pulses so that the user cannot predict accurately the specific haptic feedback sequence that will be generated by the vibration element 144. In another embodiment, the haptic feedback sequence is a pulsed vibration having from two to five vibration pulses of different durations. An exemplary pattern includes a first pulse having a 0.5 second duration followed by a 0.5 second pause, a second pulse having a 1.0 second duration followed by a 0.5 second pause, a third pulse having a 0.25 second during followed by a 0.25 second pause, and a fourth pulse having a 0.25 second duration. In response to receiving the activation signal, the vibration element 144 is configured to generate a haptic feedback sequence having any number of pulses of any random duration interspersed with pauses each having a random duration. The random or variable haptic feedback sequences prevent the user from subconsciously blocking out the haptic feedback generated by the pendant system 100. That is, since the haptic feedback is typically different each time it is generated, the typical user consciously recognizes the haptic feedback without becoming accustomed to the haptic feedback.

Moreover, in some embodiments, the vibration element 144 is configured to generate the haptic feedback with multiple levels of intensity. The levels of intensity of the haptic feedback are determined by the angular velocity with which the unbalanced mass 180 is rotated by the motor 172. For example, a first level of intensity of the haptic feedback corresponds to a first angular velocity (i.e. a first rotational speed) of the unbalanced mass 180, and a second level of intensity of the haptic feedback corresponds to a second angular velocity (i.e. a second rotational speed) of the unbalanced mass 180. The second rotational speed is greater than the first rotational speed, and the second level of intensity is greater than the first level of intensity. The pendant 104 is configured to generate a predetermined number of the levels of intensity, and the predetermined number is from one to ten. In some embodiments, the wearer selects the level of intensity of the haptic feedback generated by the vibration element 144 to create a customized haptic feedback level that is based on the wearer's particular body type and sensitivity level.

Next, in block 412 of the method 400, the user performs a re-centering activity after feeling the randomly generated haptic feedback. The re-centering activity may include taking deep breaths, thinking of or reciting a prayer, and/or remembering to focus on their spirituality and faith. By re-centering, the user is prevented from getting caught in the chaos of the day and is more likely to be operating from a balanced state. The pendant system 100 operates without user intervention and without being noticeable by nearby observers. Moreover, the re-centering activity may include something as simple a quick thought to realign the user's focus, thereby ensuring that the pendant system 100 is low burden and low maintenance.

To assist and/or to supplement the user in performing the re-centering activity (should the user choose to perform the re-centering activity), the method 400, in some embodiments, includes activating the display unit 204 of the smartphone 112 when the haptic feedback is generated (i.e. when the controller 168 activates the vibration element 144). For example, in one embodiment, the display unit 204 shows the smartphones "lock screen" that includes notifications from an application (i.e. an "app") associated with the pendant system 100 that is stored and run on the smartphone 112. The notification, may be fully visible to the user without the user having to unlock the smartphone 112. The notification includes instructions or reminders regarding the re-centering activity, such as a suggestion to recite mentally a prayer and/or a suggestion to perform a relaxing breathing exercise. In another embodiment, the user unlocks the smartphone 112, and the app displays the prayer data 232 that corresponds to the full text of a prayer and/or the reminder data 236 that includes a breathing exercise on the display unit 204. The notification and the app may also cause the display unit 204 to display any other user-created data, such as inspirational words and pictures of friends, family, loved ones, and pets.

In addition to activating randomly the vibration element 144, the pendant system 100 may further activate the vibration element 144 based on the heartrate data 240 generated by the heartrate sensor 152 of the pendant 104. As noted above, when the necklace 108 is worn by the user, the pendant 104 is typically against the user's chest. Such a position places the electrodes 188, at least intermittently, against the user's skin to sense the user's heartrate. The sensed heartrate is stored as the heartrate data 240. The pendant 104 transmits the heartrate data 240 to the smartphone 112 for processing.

When the smartphone 112 receives the heartrate data 240, the controller 224 compares the user's heartrate to a predetermined heartrate range. When the user's heartrate is outside of the predetermined heartrate range, the smartphone 112 takes no action based on the heartrate data 240. When, however, the heartrate data 240 is within the predetermined heartrate range for a predetermined time period, the controller 224 generates an activation signal that is transmitted to the pendant 104 for activating the vibration element 144. In a specific exemplary embodiment, the predetermined heartrate range is from 130 beats per minute to 150 beats per minute, and the predetermined time period is two minutes. The predetermined heartrate range is an elevated heartrate range that tends to indicate that the user is stressed, excited, or nervous. Thus, when the user's heartrate is within the predetermined heartrate range for the duration of the predetermined time period, the user may benefit from a reminder (i.e. the haptic feedback) to calm down and re-center their thoughts. The predetermined heartrate range is customizable depending on the sex, age, and physical fitness level of the user.

In another embodiment of the pendant system 100 and the method 400, the pendant system 100 does not include the smartphone 112 and includes only the pendant 104 and the necklace 108. In such an embodiment, the activation signals for activating the vibration element 144 are generated randomly by the controller 168 of the pendant 104 instead of by the smartphone 112. The pendant system 100, in such an embodiment, operates entirely without the need for the smartphone 112. Moreover, in embodiments of the pendant system 100 that include the smartphone 112, the controller 168 of the pendant 104 is configured to generate the activation signals when the smartphone 112 is out of range or otherwise temporarily electronically disconnected from the pendant 104. For example, if the smartphone 112 is powered off, the controller 168 of the pendent 104 identifies the disconnection of the smartphone 112 and switches to generating the activation signals instead of waiting for the activation signals to be transmitted to the transceiver 148 from the smartphone 112.

In another embodiment of the pendant system 100, the pendant 104 is configured to generate haptic feedback according to a scheduled time table instead of the random haptic feedback. The scheduled haptic feedback is generated in addition to or in alternative to the random haptic feedback described above. According to the scheduled haptic feedback, the user operates the smartphone 112 to program (i) certain times or time windows during which the activation signals for the vibration element 144 are generated, and (ii) certain times or time windows during which the activation signals for the vibration element 144 not generated. For example, some users may desire in advance to receive haptic feedback following a particular event that occurs at a known time. The event may be stressful meeting or other distraction, and the user benefits from receiving the haptic feedback at a scheduled time and date after the stressful meeting as a reminder to re-center their thoughts. Moreover, the user may follow a known sleep schedule, and the user programs the pendant system 100 so that activation signals for the vibration element 144 are not generated during the times that the user is typically sleeping, resting, or otherwise desiring to be undisturbed. The pendant system 100 can be programmed to generate or to not generate the activation signals for the vibration element 144 at any time or time window through the day.

The pendant system 100 is operable with dedicated apps and other existing apps. As used herein, a dedicated app, is a program run on the smartphone 112 that was specifically prepared for generating the activation signals for the vibration element 144 and for displaying data configured to assist the user in re-centering their thoughts. An existing app, as used herein, is a program run on the smartphone 112 that was not specifically prepared for generating the activating signals. The pendant system 100 is configured to integrate with existing apps for generating the activation signals for the vibration element 144. For example, after the smartphone 112 generates an activation signal, the controller 224 causes an existing app to auto-open and to display data that helps the user to re-center their thoughts. Examples of existing apps that integrate well with the pendant system 100 are meditation apps and breathing apps.

Figure 5:
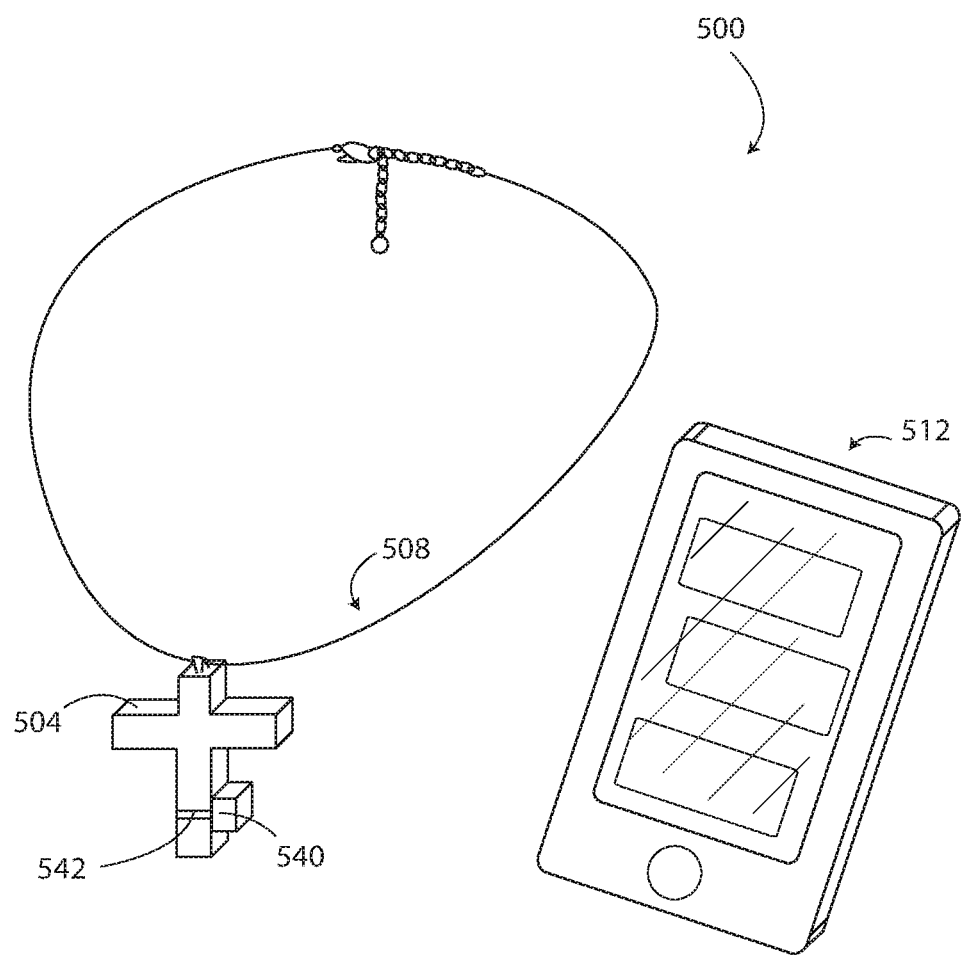
FIG. 5 is a block diagram of an accessory system, as disclosed herein, that includes a housing mounted on a pendant of a necklace.

As shown in FIG. 5, an accessory system 500 for a pendant 504 of a necklace 508 includes a housing 540 mounted on the pendant 504. The housing 540, when mounted on the pendant 504, provides the pendant 504 with the haptic feedback features of the pendant 140 of the pendant system 100. The accessory system 500 also includes a smartphone 512.

The housing 540 of the accessory system 500 includes a mounting structure 542. Additionally, the housing 540 includes a vibration element 544, a transceiver 548, a heartrate sensor 552, a first input 556, a second input 560, and a battery 564 each operably connected to a controller 568. The mounting structure 542 is configured to connect the housing 540 to the pendant 504 of the necklace 508. In the exemplary embodiment of FIG. 5, the housing 540 is mounted to a cross-shaped pendant 504 that is different from the cross-shaped pendant 104 shown in FIG. 1. Specifically, the pendant 504 of FIG. 5 is a decorative item only and includes no electronic components. The mounting structure 542 is configured to connect the housing 540 to a pendant of any shape and is provided as an elastic band, a metal strap, and/or adhesive, for example. The mounting structure 542 is configured to permanently or removably connect the housing 540 to the pendant 504. When the housing 540 is permanently connected to the pendant 504, the housing 540 cannot be removed from the pendant 504 without destroying at least one of the housing 540 and the pendent 504. When the housing 540 is removably connected to the pendent 504, the housing 540 can be removed and re-mounted on the pendant 504, as desired by the user. The housing 540 is configured as a weight to pull the pendant 504 against the user to ensure that the user feels the haptic feedback. Accordingly, the position of the housing 540 on the pendant 504 is selected to position properly the pendant 504 against the user taking into consideration the pull imposed on the pendant by the housing 504.

The vibration element 544 is substantially the same as the vibration element 144. The vibration element 544 is configured to generate haptic feedback to a user of the accessory system 500 according to at least one of the random or the scheduled haptic feedback approaches discussed above. In particular, the vibration element 544 generates vibrations that transfer to the housing 540, the pendant 504, and the wearer of the pendant 504 and the necklace 508. The vibration element 544 includes an electric motor 572 with a corresponding driveshaft 576. An unbalanced mass 580 is mounted on the driveshaft 576. In other embodiments, the housing 540 includes any other suitable type of vibration element 544. The vibration element 544 is configured to generate any type of haptic feedback sequence with a user selectable intensity level, in the same manner as the vibration element 144.

The transceiver 548, which is also referred to as a wireless transmitter and receiver, is configured to transmit wirelessly data from the housing 540 to the smartphone 512 and to receive wirelessly data from the smartphone 512. The transceiver 548 sends and receives data using a wireless local area network ("Wi-Fi"), a personal area network, and/or any other wireless network. Accordingly, the transceiver 548 is compatible with any desired wireless communication standard or protocol including, but not limited to, Near Field Communication ("NFC"), IEEE 802.11, and IEEE 802.15.1 ("Bluetooth®"), for example.

Figure 6:
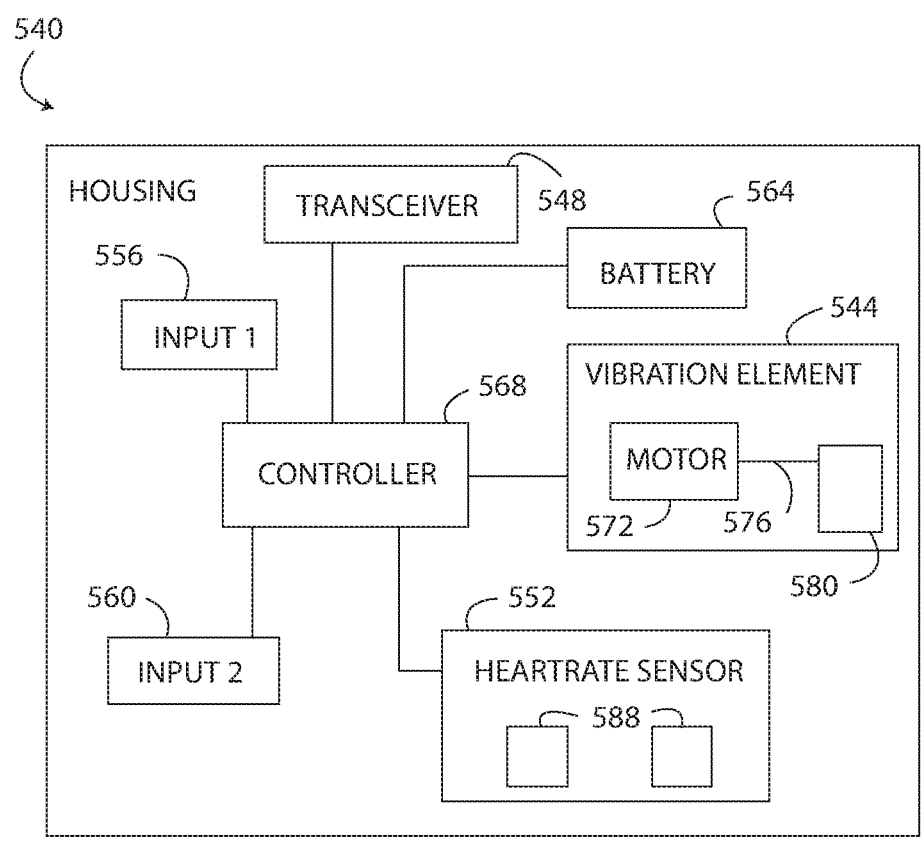
FIG. 6 is a block diagram of the housing of FIG. 5.

With continued reference to FIG. 6, the heartrate sensor 552 is configured to generate heartrate data corresponding to a measured heartrate of a person wearing the housing 540, the pendant 504, and the necklace 508. The heartrate sensor 552 includes electrodes 588 that are positioned against or near the skin of the user. The heartrate sensor 552 senses a pulse of the user and/or senses electrocardiogram data (EKG data) of the user. In some embodiments, the housing 540 does not include the heartrate sensor 552.

The first input 556 is a user interface device for activating and deactivating the housing 540. In particular, the first input 556 is a switch or a button that is moved or pressed by the user of the accessory system 500. For example, when the first input 556 is pressed a first time, the accessory system 500 "powers on" and is activated, and when the first input 556 is pressed a second time, the accessory system 500 "powers off" and is deactivated.

The second input 560 is another user interface device for "pairing" the housing 540 to the smartphone 512. In particular, the second input 560 is a switch or a button that is moved or pressed by the user of the accessory system 500. For example, when the second input 560 is pressed, the housing 540 and the smartphone 512 share data wirelessly for pairing the housing 540 with the smartphone 512.

The battery 564 is a rechargeable lithium-ion polymer (Li-ion polymer or LiPo) battery cell having a nominal voltage of about 3.7 V. In other embodiments, the battery 564 is a nickel-cadmium (NiCd), nickel-metal hydride (NiMH), lithium-ion (Li-ion), or any other desired rechargeable battery architecture. In one embodiment, the battery 564 requires recharging only after five to seven days of continuous use of the accessory system 500. Thus, the housing 540 requires infrequent recharging as a convenience to the user. In another embodiment, the battery 564 is a button cell battery, also referred to as a watch battery, and the housing 540 has a corresponding structure to permit user removal and user replacement of the button cell battery 564.

The controller 568 of the housing 540 is configured to execute program instructions (i.e. software) for operating the system 500 to generate haptic feedback to the user, to transmit and receive data from the smartphone 512, and to recharge the battery 564. Additionally, in some embodiments, the controller 568 generates activation signals for activating the vibration element 544. The controller 568 is provided as at least one microcontroller and/or microprocessor.

The smartphone 512 is an exemplary remote electronic device that is operably connected to the housing 540 of the accessory system 500. The smartphone 512 is the same as the smartphone 112.

The housing 540 of the accessory system 500 operates the same as the pendant 140 of the pendant system 100. Specifically, in response to receiving an activation signal from the smartphone 512 or generating an activation signal with the controller 568, the housing 540 is configured to activate randomly the vibration element 544 in order to generate the haptic feedback. The haptic feedback reminds the user to re-center on matters of spiritual importance or any other matter of importance to the user. The accessory system 500 is configured for use with dedicated apps and existing apps in the same manner as the pendant system 100.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A pendant system, comprising:
    a pendant configured to mount on a necklace, the pendant including a housing;
    a vibration element located within the housing and configured generate haptic feedback when activated;
    a controller located within the housing and configured to activate the vibration element randomly; and
    a remote electronic device operably connected to the controller and including a display unit, the remote electronic device configured to activate the display unit when the controller activates the vibration element,
    wherein the activated display unit is configured to display data corresponding to prayers.

2. The pendant system of claim 1, wherein the housing is a crucifix.

3. The pendant system of claim 1, wherein the housing is a cross, a peace sign, or a Star of David.

4. The pendant system of claim 1, further comprising:
    a transceiver located within the housing and configured to operably connect to the remote electronic device,
    wherein the remote electronic device generates activation signals randomly,
    wherein the activation signals are transmitted from the remote electronic device to the transceiver, and
    wherein the transceiver is configured to send the received activation signals to the controller for activating the vibration element randomly.

5. The pendant system of claim 4, wherein the remote electronic device is a smartphone.

6. The pendant system of claim 1, wherein the housing is waterproof, such that the pendant is wearable while swimming or in a shower without damaging at least the controller and the vibration element.

7. The pendant system of claim 1, wherein activating the vibration element randomly includes activating the vibration element randomly a predetermined number of times within a predetermined time period.

8. The pendant system of claim 1, further comprising:
    a heartrate sensor located at least partially within the housing and configured to generate heartrate data corresponding to a heartrate of a person wearing the necklace,
    wherein the controller is configured to compare the heartrate data to a predetermined heartrate range, and
    wherein the controller is configured to activate the vibration element when the heartrate data is within the predetermined heartrate range for a predetermined time period.

9. A pendant system, comprising:
    a pendant configured to mount on a necklace, the pendant including a housing;
    a vibration element located within the housing and configured generate haptic feedback when activated;
    a controller located within the housing and configured to activate the vibration element randomly; and
    a remote electronic device operably connected to the controller and including a display unit, the remote electronic device configured to activate the display unit when the controller activates the vibration element,
    wherein the remote electronic device is configured to store user-created data, and
    wherein the activated display unit is configured to display the user-created data.

10. An accessory system for a pendant of a necklace, comprising:
    a housing;
    a mounting structure configured to mount the housing on the pendant;
    a vibration element located within the housing and configured to generate haptic feedback when activated;
    a controller located within the housing and configured to activate the vibration element randomly; and
    a remote electronic device operably connected to the controller and including a display unit, the remote electronic device configured to activate the display unit when the controller activates the vibration element,
    wherein the remote electronic device is configured to store user-created data, and
    wherein the activated display unit is configured to display the user-created data.

11. The accessory system of claim 10, further comprising:
    a transceiver located within the housing and configured to operably connect to the remote electronic device,
    wherein the remote electronic device generates activation signals randomly,
    wherein the activation signals are transmitted from the remote electronic device to the transceiver, and
    wherein the transceiver is configured to send the received activation signals to the controller for activating the vibration element randomly.

12. The accessory system of claim 11, wherein the remote electronic device is a smartphone.

13. The accessory system of claim 10, wherein the housing is waterproof, such that the housing is wearable while swimming or in a shower without damaging the controller or the vibration element.

14. The accessory system of claim 10, wherein activating the vibration element randomly includes activating the vibration element randomly a predetermined number of times within a predetermined time period.

15. The pendant system of claim 9, wherein the housing is a crucifix.

16. The pendant system of claim 9, wherein the housing is a cross, a peace sign, or a Star of David.

17. The pendant system of claim 9, further comprising:
    a transceiver located within the housing and configured to operably connect to the remote electronic device,
    wherein the remote electronic device generates activation signals randomly,
    wherein the activation signals are transmitted from the remote electronic device to the transceiver, and
    wherein the transceiver is configured to send the received activation signals to the controller for activating the vibration element randomly.

18. The pendant system of claim 17, wherein the remote electronic device is a smartphone.

19. The pendant system of claim 9, wherein activating the vibration element randomly includes activating the vibration element randomly a predetermined number of times within a predetermined time period.

20. The accessory system of claim 10, wherein the mounting structure includes an elastic band and/or an adhesive to mount the housing on the pendant.

\* \* \* \* \*